United States Patent [19]

Chikawa et al.

[11] Patent Number: 5,153,000
[45] Date of Patent: Oct. 6, 1992

[54] PHOSPHATE, LIPOSOME COMPRISING THE PHOSPHATE AS MEMBRANE CONSTITUENT, AND COSMETIC AND LIPOSOME PREPARATION COMPRISING THE LIPOSOME

[75] Inventors: Yoshiko Chikawa, Wakayama; Katsumi Kita, Izumisano; Mitsuharu Masuda, Wakayama; Tomihiro Kurosaki, Osaka; Takashi Itoh, Wakayama; Noriko Inoue, Funabashi; Haruya Kato, Funabashi; Takashi Imamura, Funabashi; Yasuo Ishii, Wakayama; Yoshitaka Kokusho, Kunitachi; Akira Tsunoda, Fussa; Shigeaki Kato, Hino, all of Japan

[73] Assignees: Kao Corporation, Tokyo; Meito Sangyo Co., Ltd., Nagoya, both of Japan

[21] Appl. No.: 437,099

[22] Filed: Nov. 16, 1989

[30] Foreign Application Priority Data

Nov. 22, 1988 [JP] Japan ................................ 63-295653

[51] Int. Cl.$^5$ ..................... A61K 37/22; A61K 9/127; B01J 13/02
[52] U.S. Cl. .................................... 424/450; 424/401; 424/417; 264/4.1; 558/160; 558/163; 558/164
[58] Field of Search .................... 424/450, 401, 417; 260/403; 264/4.1; 558/160, 163, 164

[56] References Cited

U.S. PATENT DOCUMENTS

| | | | |
|---|---|---|---|
| 4,089,801 | 5/1978 | Schneider | 424/450 |
| 4,217,344 | 8/1980 | Vanlerbeighe | 424/450 |
| 4,220,611 | 9/1980 | Wolf | 260/929 |
| 4,247,411 | 1/1981 | Vanlerberghe | 424/450 |
| 4,426,330 | 1/1984 | Sears | 260/403 |
| 4,619,794 | 10/1986 | Hauser | 424/450 |
| 4,830,857 | 5/1989 | Handjani | 424/450 |
| 4,855,090 | 8/1989 | Wallach | 424/450 |
| 4,963,367 | 10/1990 | Ecanow | 424/485 |
| 5,013,556 | 5/1991 | Woodle et al. | 424/450 |

FOREIGN PATENT DOCUMENTS

| | | |
|---|---|---|
| 125039 | 11/1984 | European Pat. Off. . |
| 220797 | 5/1987 | European Pat. Off. . |
| 288255 | 10/1988 | European Pat. Off. . |
| 8707530 | 12/1987 | World Int. Prop. O. . |

Primary Examiner—Thurman K. Page
Assistant Examiner—G. S. Kishore
Attorney, Agent, or Firm—Oblon, Spivak, McClelland, Maier & Neustadt

[57] ABSTRACT

A novel monophosphate and a novel diphosphate prepared by a phosphatidyl transfer reaction of a phospholipid and an alcohol in the presence of phospholipase D are disclosed. The phosphates can independently or together form small and stable liposomes which can include active components therein. Cosmetic compositions comprising these phosphates or liposomes penetrate well into the hair and the skin, and exhibit long-lasting excellent moisture-retaining, beauty, skin-activation effects.

5 Claims, 2 Drawing Sheets

PHOSPHATE, LIPOSOME COMPRISING THE PHOSPHATE AS MEMBRANE CONSTITUENT, AND COSMETIC AND LIPOSOME PREPARATION COMPRISING THE LIPOSOME

BACKGROUND OF THE INVENTION

1. Field of the Invention:

The present invention relates to a novel phosphate, a liposome comprising the phosphate as a membrane costitutent, and a cosmetic or a liposome preparation comprising the liposome.

2. Description of the Background Art:

Liposomes consisting of spheres of single- or multi lipid bilayers are drawing a great deal of attention as carriers of various medicines. Liposomes comprising an active component are used as cosmetic ingredients. In order to promote penetration into the hair and the skin, to increase the effect of active components encapsulated in liposomes, and to ensure a prolonged effect, liposomes incorporated into cosmetic composition must be small-sized vesicles which are stable over a long period of time. Natural phospholipids, cholesterols, and the like are known as liposome producing agents. A simple addition of these liposome producing agents to water will result in multilamella large liposomes having a vesicle size of about 1-5 μm. These liposomes have problems such as difficulty in penetration through the skin and the like. Conventionally known methods of producing liposomes are a method of using ultrasonic radiation, a method of removing a surface-active agent from a mixed system of the surface-active agent and a liposome, a method of charging an ethanol solution of a liposome-producing agent into water, the reverse micelle method, and the like [e.g. L. S. Rao, *Liposome Technology*, edited by G. Gregoriadis, CRC Press, USA (1984)].

These methods, however, have problems such as the incapability of a large-scale production, difficulty of producing a high concentration liposome, and the like. Besides, small unilamella vesicles produced by these methods tend to become large multilamella vesicles with the passage of time.

As a means of resolving such problems, for example, a method of producing a small liposome having a 30 nm radius by simply charging a didodecyldimethylammonium cation having a hydroxyl ion or an acetate ion as a counter ion into water has been proposed [Ninham, Evans, et al., *Faraday Discuss. Chem. Soc.*, 81, (1986)].

This method, however, also has problems such as an extremely narrow concentration range capable of producing small size liposomes, which makes it difficult to incorporate the liposomes into cosmetic composition containing many compounds, strictly limited conditions under which an active component is encapsulated in liposomes, the use of a cationic surface-active agent as a liposome-producing agent which is undesirable to incorporate into cosmetic compositions in a large amount, and the like.

In this situation, development of small-sized, stable liposomes which are capable of encapsulating active components therein and which can easily be produced in a large scale has been desired. There has also been a strong desire for the development of cosmetic compositions which can exhibit their effects for a long period of time while imparting only low irritation to living bodies.

As a result of extensive studies, the present inventors found that novel diphosphate represented by the formula (II) shown below could be prepared at a high yield from readily available raw materials by a simple reaction and procedure. The inventors further found that the diphosphate of formula (II) and a monophosphate of the formula (I) also shown below could be produced at a large, industrial scale, that these phosphates could independently or together form small and stable liposomes which can include active components therein, and further that cosmetic compositions comprising these phosphates penetrate well into the hair and the skin, and exhibit long-lasting excellent moisture-retaining, beauty, skin-activation effects. In addition, the inventors discovered a liposome preparation comprising a liposome which includes active components therein. Such findings have led to the completion of the present invention.

SUMMARY OF THE INVENTION

Accordingly, an object of the present invention is to provide a liposome comprising as its membrane constituents a monophosphate represented by the formula (I), a diphosphate represented by the formula (II), or both,

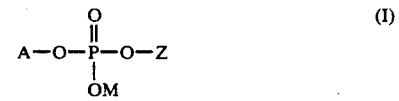

wherein A represents the following group (i), (ii), or a mixture thereof:

wherein $R^1$ and $R^2$ may be the same or different and individually represent a group $-OCOR^3$, $-OR^4$, or a mixture thereof wherein $R^3$ and $R^4$ may be the same or different and individually represent an alkyl or alkenyl group having 6-32 carbon atoms, or $R^1$ and $R^2$ may together form the group,

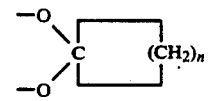

wherein n is an integer of 11-19; M represents a hydrogen atom, an alkali metal, an alkaline earth metal, an ammonium, alkylammonium, or alkanolammonium group; and Z represents a residue of either one of the following groups (1)-(5) from which one primary hydroxyl group is removed, (1) a mono- or polyether group represented by the formula $HO-(Y-O-)_m-H$, wherein m is an integer of 2-50, and Y represents an alkylene or substituted alkylene group having 2-4 carbon atoms, (2) a polyglycerol group having a condensation degree of 2-50, (3) a monosaccharide having 5-7 carbon atoms and at least two primary hydroxyl groups or a disaccharide which is composed of the monosaccharide units, (4) a sugar alcohol having 4-7 carbon atoms, or (5) a monosaccharide having 5-7 carbon atoms and one primary hydroxyl group, which may be substituted by an amino or acetyl amino group, a disaccharide which is composed of the monosaccharide units, or a glycoside derived from the monosaccharide or disaccharide;

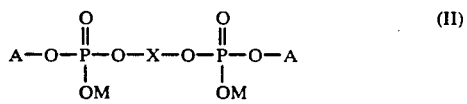

(II)

wherein A and M have the same meaning as defined in formula (I), and X represents a residue of either one of the following groups (1)-(3) from which two primary hydroxyl groups are removed, (1) a mono- or polyether group represented by the formula HO—(Y—O—)$_m$—H, wherein m is an integer of 2-50 and Y represents an alkylene or substituted alkylene group having 2-4 carbon atoms, (2) a polyglycerol group having a condensation degree of 2-50, (3) a monosaccharide having 5-7 carbon atoms and at least two primary hydroxyl groups or a disaccharide which can be decomposed into such a monosaccharide.

Another object of the present invention is to provide a cosmetic composition comprising a monophosphate of the above formula (I) or a diphosphate of the above formula (II), or both.

Still another object of the present invention is to provide a diphosphate of the above formula (II).

Other objects, features and advantages of the invention will hereinafter become more readily apparent from the following description.

DETAILED DESCRIPTION OF THE INVENTION AND PREFERRED EMBODIMENTS

Figure 1:
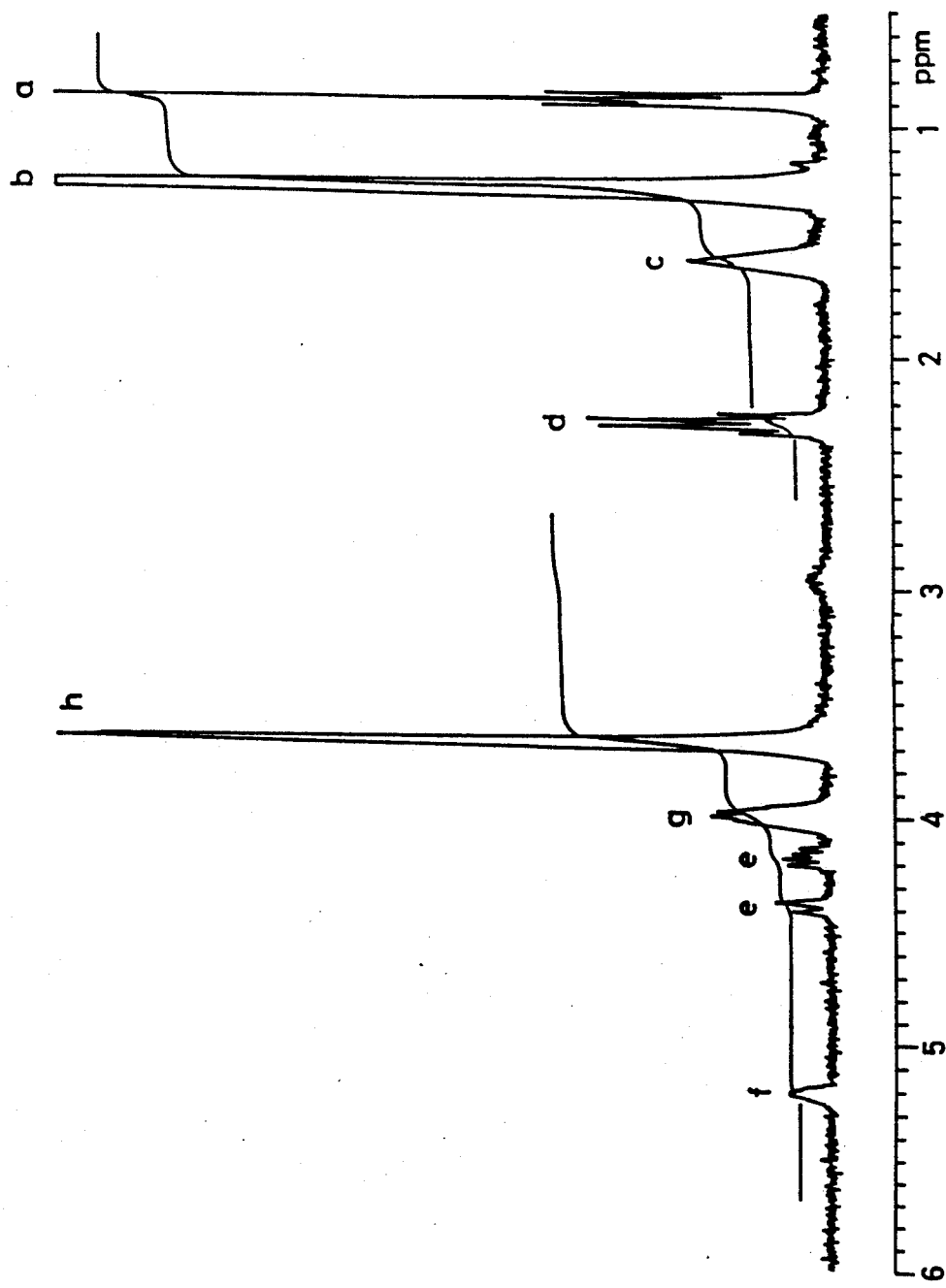
FIG. 1 is a drawing showing an NMR spectrum of diphosphatidyl PEG400 prepared in Example 1 and FIG. 2 is a drawing showing an IR spectrum of the same compound.

The group A of formula (I) or (II) may be either the above-mentioned group (i) or (ii). Also, the mono-or diphosphate of formula (I) or (II) may be a mixture of the phosphates having a different group A selected from (i) and (ii). Alkyl or alkenyl groups represented by $R^3$ and $R^4$ may be such groups as hexyl, octyl, decyl, dodecyl, tetradecyl, hexadecyl, octadecyl, eicosyl, docosyl, tetracosyl, hexacosyl, octacosyl, triacontyl, dotriacontyl, 2-ethylhexyl, octadienyl, decadienyl, dodecadienyl, tetradecadienyl, hexadecadienyl, octadecadienyl, eicosadienyl, docosadienyl, tetracosadienyl, hexacosadienyl, octacosadienyl, triacontadienyl, dotriacontadienyl, hexadecatrienyl, octadecatrienyl, eicosatrienyl, docosatrienyl, tetracosatrienyl, hexacosatrienyl, octacosatrienyl, triacontatrienyl, dotriacontatrienyl, eicosatetraenyl, docosatetraenyl, tetracosatetraenyl, hexacosatetraenyl, octacosatetraenyl, triacontatetraenyl, dotriacontatetraenyl, docosapentaenyl, tetracosapentaniel, hexacosapentaniel, octacosapentaniel, triacontapentaniel, dotriacontapentaniel, docosahexaniel, tetracosahexaniel, hexacosahexaniel, octacosahexaniel, triacontahexaniel, dotriacontahexaniel, or the like.

As specific examples of the group represented by M of formulae (I) and (II), which generically represents a hydrogen atom, an alkali metal, an alkaline earth metal, an ammonium, alkylammonium, or alkanolammonium group, given, beside hydrogen and ammonium, are potassium, lithium, sodium, beryllium, magnesium, calcium, strontium, barium, triethanolammonium, trimethylammonium, triethylammonium, and the like.

Examples of alkylene groups represented by Y in the mono- or polyether group of formula HO—(—Y—O—)$_m$—H described in item (1) include such groups as ethylene, propylene butylene, 1-methylpropylene, and the like. Among the integer m which is generically 2-50, an integer of 4-50 is preferable, with the range 4-20 being particularly preferable. Specific examples of polyethers are polyethylene glycol having an average molecular weight of 400 (hereinafter referred to as PEG400), polyethylene glycol having an average molecular weight of 600 (hereinafter referred to as PEG600), polypropylene glycol having an average molecular weight of 200 (hereinafter referred to as PEG200), and the like.

Among the condensation degree of 2-50 of the polyglycerol group described in item (2), a range of 4-50 is preferable, with the particularly preferable range being 4-20. Specific examples of polyglycerols include polyglycerol having an average molecular weight of 500 (hereinafter referred to as PG500), polyglycerol having an average molecular weight of 750 hereinafter referred to as PG750), and the like.

Given as examples of monosaccharides described in item (3) having 5-7 carbon atoms and at least two primary hydroxyl groups are xylulose, ribulose, sorbose, psicose, tagatose, sedoheptulose, glucoheptulose, mannoheptulose, and the like, and of examples of the disaccharides composed of such monosaccharide units are sucrose, maltose, cellobiose, trehalose, lactose, and the like.

Examples of sugar alcohols described in item (4) include erythritol, ribitol, arabitol, xylitol, sorbitol, mannitol, galactitol, sedoheptitol, perseitol, and the like.

Examples of saccharides and glycosides described in item (5); monosaccharides having 5-7 carbon atoms and one primary hydroxyl group, which may be substituted by an amino or acetyl amino group, disaccharides which are composed of the monosaccharide units, or a glycoside derived from the monosaccharide or disaccharide; include arabinose, ribose, 2-deoxyribose, lyxose, xylose, α- or β-methylxyloside, 2-O-methylxylose, β-methylarabinoside, 2-deoxyglucose, glucose, galactose, mannose, talose, melibiose, gentiobiose, α- or β-methylgalactoside, α- or β-methylglucoside, α- or β-methylmannoside, 3-O-methylglucose, 1-thio-β-galactose, β-thioglucose, 5-thioglucose, methyl-β-thiogalactoside, ethyl-β-thioglucoside, 2-deoxygalactose, α-chloralose, α-glucoheptose, galactosamine, glucosamine, mannosamine, N-acetylgalactosamine, N-acetylglucosamine, N-acetylmannosamine, methyl-3-amino-3-deoxy-β-glucoside, methyl-3-amino-3-deoxy-β-mannoside, streptozotocin, salicin, arbutin, 1-O-phenyl-α- or β-glucoside, 1-O-phenyl-α- or βgalactoside, o-nitrophenyl-α- or β-galactoside, m-nitrophenyl-α- or β-galactoside, p-nitrophenyl-α- or β-galactoside, p-nitrophenyl-α- or β-glucoside, o-nitrophenyl-α- or β-glucoside, p-nitrophenyl-α- or β-mannoside, p-nitrophenyl-1-thio-β-galactoside, o-nitrophenyl-1-thio-β-galactoside, p-nitrophenyl-1-thio-β-glucoside, o-nitrophenyl-β-xyloside, p-nitrophenyl-α- or β-xyloside, phenyl-α- or β-thiogalactoside, mandelonitrileglucoside, and the like.

Among the phosphates of the present invention, preferable phosphates are those in which A in formula (I) or (II) is the formula (i) group and in which $R^1$ and $R^2$ are a combination of groups selected from lauroyl, myristoyl, palmitoyl, stearoyl, oleoyl, lynoleoyl, lynolenoyl, arachidonoyl, docosahexanoyl, eicosapentanoyl, and the like. Another preferable phosphates are those in which A in formula (I) or (II) is a mixture of groups having the same distribution with those of natural phospholipids derived from egg yolk, soy bean, or the like. They are, for example, mono- or diphosphatidyl PEG400, mono- or diphosphatidyl PEG600, mono- or diphosphatidyl PPG200, mono- or diphosphatidyl PG500, mono- or diphosphatidyl PG750, or their mixtures.

A phosphate used in the present invention can be prepared according, for example, to the following reaction scheme.

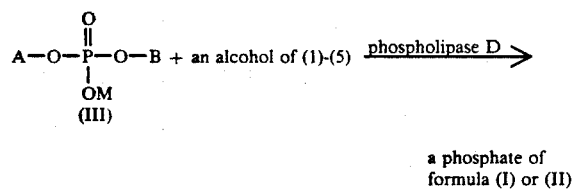

a phosphate of formula (I) or (II)

wherein A and M have the same meanings as defined above and B represents a residue of an organic base having not more than 4 carbon atoms and a primary hydroxyl group and from which a hydroxyl group is removed.

According to the above reaction formula, a phosphate of formula (I), (II), or a mixture thereof is prepared by a phosphatidyl transfer reaction, desirably in a solvent, of a natural or synthetic phospholipid (III) and an alcohol of (1)–(5) in the presence of phospholipase D.

A phospholipid (III) and an alcohol of (1)–(5) can be selected depending on the target phosphate. There are no specific limitations as to their types. Given as examples of phospholipids (III) are egg yolk lecithin, soy bean lecithin, synthetic lecithins, and the like, and as examples of alcohols are PEG400, PEG600, PPG200, PG500, PG750, fructose, and the like.

Also, there are no specific limitations as to the source from which a phospholipase D which is used in the reaction is derived. For example, phospholipase DM derived from a microorganism belonging to the genus such as *Nocardiopsis sp.* No. 779 (FERM-P No. 6133; the international deposit number BP 512 under the Budapest Treaty) or phospholipase DM derived from a microorganism belonging to the genus such as *Actinomadura sp.* No. 362 (FERM-P No. 6132; the international deposit number BP 511 under the Budapest Treaty).

A typical example of a solvent which can be used in the reaction is a mixed solvent of an organic solvent such as ether, ethyl acetate, benzene, chloroform, or the like and a suitable aqueous solvent. A suitable additive which may promote the activity of phospholipase D or which can help to stabilize the enzyme can be added to the aqueous solvent. Such suitable additives include proteins such as albumin, casein, and the like, buffer agents such as acetic acid, citric acid, phosphoric acid, and the like, neutral salts such as calcium chloride and the like.

A molar ratio of the compounds to be reacted and amounts of phospholipase D and the solvent may be determined from among suitable ranges. Generally, a suitable range of the molar ratio of a phospholipid (III) and a polyhydric alcohol of (1)–(5) is for one mole of a phospholipid (III) 0.1–100 moles of a polyhydric alcohol. An amount of a phospholipase D to be used is about 10–100,000 units, preferably 100–1,000 units, per 1 g of phospholipid (III). An amount of a solvent which may be used is about 2–100 times by weight of the phospholipid (III). The reaction temperature and the reaction time can be suitably determined. Preferable range is about 20°–60° C. and 1–72 hours.

In the above reaction, a phosphatidyl group transfer is effected on the primary —OH group of an alcohol of (1)–(5) by phospholipase D. Accordingly, phosphates of the present invention are usually obtained as a mixture of monophosphates of formula (I) and diphosphates of formula (II).

In the present invention, such a phosphate mixture can be used as is, or as mono- or diphosphates after their separation from the mixture. When used as a mixture, a preferable ratio of the monophosphates of formula (I) and the diphosphates of formula (II) in the mixture is in the range of 1:99–99:1 by weight. Separation of phosphates from the mixture can be performed by means of solvent fractionation using an organic solvent such as acetone, methanol, ethanol, isopropanol, or the like, separating liquid method, silica gel chromatography, high performance liquid chromatography, and the like.

Monophosphates of formula (I) and diphosphates of formula (II) thus prepared can produce stable, small size liposomes. It is desirable in the preparation of such small-size liposomes to incorporate a water-soluble salt and/or a surface-active agent [hereinafter collectively referred to as "components (b)"]into the monophosphates of formula (I) and/or diphosphates of formula (II) [these are hereinafter collectively referred to as "phosphates (a)"].

Organic or inorganic salts having a solubility in water of $10^{-4}$ M or greater at room temperature are preferable as a water-soluble salt. Such inorganic salts include salts of hydrochloric acid, nitric acid, sulfuric acid, phosphoric acid, carbonic acid, hydrobromic acid, hydroiodic acid, or the like having an alkali metal, ammonium, or the like as a counter ion. Specific examples of preferable inorganic salts are potassium bromide, potassium chloride, potassium dihydrogenphosphate, dipotassium hydrogenphosphate, potassium sulfate, potassium iodide, potassium nitrate, lithium bromide, lithium chloride, lithium iodide, lithium nitrate, lithium sulfate, ammonium bromide, ammonium chloride, ammonium carbonate, ammonium hydrogencarbonate, ammonium dihydrogenphosphate, diammonium hydrogenphosphate, ammonium iodide, ammonium nitrate, ammonium sulfate, sodium bromide, sodium carbonate, sodium chloride, sodium hydrogencarbonate, sodium dihydrogenphosphate, disodium hydrogenphosphate, sodium nitrate, sodium phosphate, sodium sulfate, and the like. Organic salts which can be used include alkanolamine chloride, sulfate, phosphate, and the like, and salts of benzoic acid, acetic acid, salicylic acid, oxalic acid phthalic acid, gluconic acid, 1-naphthalenesulfonic acid, 2-naphthalenesulfonic acid, tartaric acid, maleic acid, malonic acid, succinic acid, fumaric acid, propionic acid, ascorbic acid, mandelic acid, malic acid, citric acid, or the like having an alkali metal or ammonium ion as a counter ion. Specific examples of preferable organic salts are triethanolammonium chloride, triethanolammonium dihydrogenphosphate, triethanolammonium sulfate, sodium benzoate, potassium benzoate, ammonium benzoate, sodium acetate, potassium acetate, ammonium acetate, sodium salicylate, potassium salicylate, ammonium salicylate, sodium oxalate, potassium oxalate, ammonium oxalate, sodium phthalate, potassium phthalate, ammonium phthalate, sodium gluconate, potassium gluconate, ammonium gluconate, ammonium 1-naphthalenesulfonate, potassium 2-naphthalenesulfonate, ammonium 2-naphthalenesulfonate, sodium 2-naphthalenesulfonate, potassium tartarate, sodium maleate, potassium maleate, sodium malonate, sodium succinate, sodium fumarate, sodium propionate, triethanolammonium propionate, sodium ascorbate, triethanolammonium ascorbate, potassium ascorbate, sodium mandelate, sodium malate, sodium citrate, potassium citrate, triethanolammonium citrate, and the like. Among these, particularly preferable salts are sodium chloride, sodium sulfate, sodium hydrogencarbonate, ammonium chloride, ammonium sulfate, sodium acetate, and the like.

In order to prepare the liposome of the present invention it is desirable to use the water-soluble salt of the component (b) and the phosphate (a) at a (a)/(b) ratio of $10^{-3}$–$10^3$, and preferably of 0.1–10. Also, it is desirable that the water-soluble salt be used at an ionic strength in water of about $10^{-4}$–1 M, preferably $10^{-3}$–0.1 M.

Surface active agents used as the component (b) may be of anionic, cationic, nonionic, or amphoteric. There are no limitations as to their types and amounts. A range of the surface-active agent to be used as the component (b) for the phosphates (a), the phosphate, in molar ratio (a)/(b), is $10^{-3}$–$10^3$, with a preferable range being about 0.5–100, and the most preferable range being about 1–10.

Given as examples of anionic surface-active agents used as a component (b) in this invention are alkyl sulfates, alkyl benzene sulfonates, stearates, palmitates, myristates, oleates, hexadecadienates, hexadecatrienates, hexadecatetraenates, octedecadienates such as linoleates, octedecatrienates such as linolenates, eicosatetraenates such as arachidates, eicosapentaenates, docosahexaenates, alkylphosphates, polyoxyethylenealkylether phosphates, polyoxyethylenealkylether sulfates, dialkylphosphates, and the like. Specific examples of preferred surface-active agents are sodium dicetylphosphate, triethanolammonium dicetylphosphate, sodium 2-decyltetradecylphosphate, and the like.

Cationic surface-active agents which can be used include, for example, monoalkyltrimethylammonium salts or dialkyldimethylammonium salts. As specific examples of such surface-active agents, cetyltrimethylammonium bromide, distearyldimethylammonium chloride, and the like are given.

Examples of nonionic surface-active agents include polyoxyethylenealkylether, polyoxyethylenealkylphenylether, glycerolalkylether, sorbitan fatty acid ester, polyoxyethylene sorbitan fatty acid ester, polyoxyethylene sorbitol fatty acid ester, glycerol fatty acid ester, polyglycerol fatty acid ester, polyoxyethylene fatty acid ester, propylene glycol fatty acid ester, polyoxyethylenealkylamine, fatty acid esters of fructose and glucose, and the like. Among these, specific examples of nonionic surface-active agents are preferably used are 9-methylheptadecylglycerylether, sorbitan monostearate, glycerol oleate, sucrose fatty acid esters, and the like. Highly hydrophobic compounds such as cholesterols can be included in the nonionic surface-active agents used in the present invention.

As examples of amphoteric surface-active agents, alkyl betaines, sulfo betaines, natural or synthetic phosphatidyl choline and phosphatidyl ethanolamine, and the like are given. Preferable compounds among these are steraryl phosphobetaine, dipalmitoyl phosphatidyl choline, and the like.

An amount of water into which the components (b), the water-soluble salt and/or the surface-active agent, are dispersed is $10$–$10^4$, preferably $20$–$10^3$, times by weight of the phosphate, the phosphates (a).

In order to produce small liposomes of the present invention, the components (a) and (b) are added to a suitable amount of water and the mixture is gently stirred. The production of liposomes can be performed at room temperature. A temperature of 40°–80° C. is, however, generally more efficient. There are no restrictions as to the manner by which the components (a) and (b) are added to water. For instance, it is possible to blend components (a) and (b) in advance or first to disperse component (b) in water followed by the addition of component (a).

Although liposomes prepared by conventional methods normally have an average diameter of 1–5 $\mu$m, it is possible to prepare liposomes having much smaller diameter, e.g. an average diameter smaller than 500 nm.

Various cosmetically acceptable active components can be incorporated into liposomes of the present invention. They may be either hydrophillic compounds, hydrophobic compounds, or mixtures of these.

Given as examples of such active components are vitamins and their derivatives such as vitamin A, vitamin $B_1$, vitamin $B_2$, vitamin $B_6$, vitamin $B_{12}$, vitamin C, vitamin D, vitamin H, vitamin K, vitamin M, vitamin Q, pantothenyl alcohol, calcium pantothenate, benzyl nicotinate, hesperidin, hesperetin, and the like; polyols and their derivatives such as glycerol, nitroglycerol, diglycerides, triglycerides, and the like; sugars and their derivatives such as glucose fructose, sorbitol, galactose, mannose, inositol, maltitol, maltose, lactose, sucrose, trehalose, cellobiose, adenylthiomethylpentose, and the like; polysaccharides and their derivatives such as hyaluronic acid, chondroitin sulfuric acid, and the like; sugar phosphates and salts thereof as well as their derivatives such as glucose-1-phosphate, glucose-6-phosphate, mannose-6-phosphate, galactose-6-phosphate, fructose-6-phosphate, glucose-1,6-diphosphate, fructose-1,6-diphosphate, fructose-2,6-diphosphate, and their sodium or potassium salts, and the like; amino acid and their derivatives such as alanine, leucine, lysine, asparagine, aspartic acid, cysteine, proline, glutamine, serine, glutamic acid, glycine, histidine, tyrosine, isoleucine, valine, and the like; cholesterols and their derivatives, ceramides and their derivatives, highly unsaturated fatty acids and their derivatives such as linoleic acid, linolenic acid, arachidonic acid, docosahexanenic acid, prostaglandin, prostacyclin, leukotriene, and the like; pyrrolidonecarboxylic acid, glycyrrhizin, bisabolol, benzalconium chloride, benzethonium chloride, paraben ester, menthol, resorcinol, hinokitiol, squalene, anthranilic acid, urea, adrenocortical hormone, estrogen, follicle-stimulating hormone, androgen, thyroxine, pituitary hormone, posterior pituitary extracts, thymic hormone, placental gonadotropin, epsilon-aminocaproic acid, allantoin, halocarbane, camphor, hydroxyammonium chloride, glutathion and its derivative, methyl-2,5-diisopropyl cinnamate, p-aminobenzoic acid ester, zinc bis(2-pyridylthiol-1-oxide), aminophenol type anti-hystamines, estradiol, ethylestradiol, salicylic acid and its derivatives, chlorodiphenhydramine, isopropylmethylphenol, chlorohexidine chloride, allantoin chlorohydroxy aluminum, homosulfamine, scopolamine, clonidine, isosorbide sulfate, 5-fluorouracil, capronium chloride, acetylcholine, and antibiotics such as penicillin, cephalosporine, streptomycin, chloromycin, and the like.

Although there are no restrictions as to the amount of the active components to be incorporated into the liposome of the present invention, it is desirable to use them in an amount of about $10^{-6}$–30% by weight based on the amount of water used in preparing the liposome.

Active components can be added by mixing them with the mixture of components (a) and (b) or by adding a solution of the active components when the liposome is prepared. Another method is to mix the active components with a brine or a dispersion of a surface-active agent and to use such a brine or dispersion in the liposome preparation.

Incorporation of phosphates (a) is important for obtaining a cosmetic composition having a superior permeability into the skin and hair and exhibiting long-lasting moisturizing, beauty, and skin-activation effects.

Although there are no restrictions as to the amount of phosphates (a) to be incorporated into the cosmetic of the present invention, it is desirable to use them in an amount of 0.01–50% by weight, particularly 0.1–40% by weight, based on the total weight of the cosmetic composition. A large-scale industrial production of low-concentration (about 0.01–10% by weight) phosphates (a) is possible. Such low-concentration phosphates can produce small-size liposomes which can contain active components therein. Cosmetics comprising such a liposome have a semi-transparent appearance. In contrast, higher concentration (about 10–50% by weight) phosphates produces a lamella phase and cosmetics comprising such phosphates exhibit a transparent gel-like appearance. This type of phosphates can produce a stable emulsion cosmetic composition by adding an oil or fat component.

The transparent gel-like cosmetic composition can be prepared by mixing the phosphates (a), water, and other components. When the liposome comprising the phosphate (a) of the present invention is to be formed in a cosmetic composition, components (b), i.e. the water-soluble base, the surface-active agent, or both, must be included. The liposome-containing cosmetic composition can be prepared according to the above-mentioned method for the preparation of the liposomes. Various active components can be added to the cosmetic composition. These active components may be present in the cosmetic composition as they are incorporated in the liposomes. The following compounds are given as examples of such active components. Vitamins and their derivatives such as vitamin A, vitamin B's, vitamin C, vitamin D, vitamin E, vitamin K, and the like; glycerol and their derivatives such as diglycerol, triglycerol, polyglycerols, monoglycerides, diglycerides, triglycerides, and the like; polyhydric alcohols such as 1,3-butylene glycol, propylene glycol, dipropylene glycol, polyethylene glycol, and the like; sugars and their derivatives such as glucose, fructose, sorbitol, galactose, mannose, inositol, maltitol, maltose, lactose, sucrose, trehalose, cellobiose, and the like; polysaccharides and their derivatives such as hyaluronic acid, chondroitin sulfuric acid, and the like; sugar phosphates and salts thereof as well as their derivatives such as glucose-1-phosphate, glucose-6-phosphate, mannose-6-phosphate, galactose-6-phosphate, fructose-6-phosphate, glucose-1,6-diphosphate, fructose-1,6-diphosphate, fructose-2,6-diphosphate, and their sodium or potassium salts, and the like; amino acid and their derivatives such as alanine, leucine, lysine, asparagine, aspartic acid, cysteine, proline, glutamine, serine, glutamic acid, glycine, histidine, tyrosine, isoleucine, valine, and the like; cholesterols and their derivatives, ceramides and their derivatives, compounds analogous to ceramides, highly unsaturated fatty acids and their derivatives such as linoleic acid, linolenic acid, arachidonic acid, docosahexanoic acid, prostaglandin, prostacyclin, leukotriene, and the like; pyrrolidonecarboxylic acid, glycyrrhizin, bisabolol, benzalconium chloride, benzethonium chloride, menthol, resorcinol hinokitiol, and the like.

There are no specific restrictions as to the amount and the concentration of the active components to be added and incorporated into the liposomes. A desirable amount is $10^{-6}$–10% by weight based on the amount of water into which the phosphates (a) and components (b) are dispersed.

The cosmetic composition of the present invention can be prepared according to a conventional method. Besides the above essential components, optional components may be added to the cosmetic composition. Such optional components include oil components (e.g. hydrocarbons, higher fatty acids, higher alcohols), water, glycerol, propylene glycol, aqueous alcohols (e.g. ethanol), polymers, coloring agents, inorganic pigments, perfumes, antioxidants, antiseptics, and the like.

As discussed above, in the cosmetic composition of the present invention in addition to the effects of phosphates (a), the effects of small-size liposomes, i.e., the stability over a long period of time and the prolonged effects of active components, can be expected. The actions inherently possessed by active components are exhibited even acutely. Furthermore, the production of the liposomes of the present invention is performed much easier and in a larger scale than conventional liposomes. Thus, the liposomes could resolve the problems with conventional liposomes for cosmetic use. When the phosphates (a) are used at a high concentration, a lamella phase is formed, thus exhibiting a beautiful appearance.

Other features of the invention will become apparent in the course of the following description of the exemplary embodiments which are given for illustration of the invention and are not intended to be limiting thereof.

EXAMPLES

Example 1

Twelve (12) g of dipalmitoyl phosphatidylcholine, 4.8 g of sodium chloride, 25 g of polyethylene glycol having an average molecular weight of 400 (hereinafter referred to as PEG 400), 1,200 units of phospholipase D having a phosphatidyl group transfer activity (e.g. that derived from Actinomadura), 120 ml of diethylether, and 100 ml of water were charged into a reactor, and the mixture was stirred at 30° C. for 24 hours. After the completion of the reaction, chloroform and methanol were added to extract lipids. To 11.5 g of precipitates thus produced 200 ml of acetone was added, and the mixture was centrifuged to remove the precipitates. The solution was concentrated to obtain 9.9 g of white crystals.

The precipitates were subjected to $^1$H-NMR and elemental analysis, and IR. As a result it was confirmed that the product was a mixture of 37% by weight of diphosphate (II), 58% by weight of monophosphate (I), 4% by weight of phosphatidylcholine, 1% by weight of phosphatic acid.

After removing the impurities which precipitate in cold acetone, the reaction mixture was condensed to dryness and refined by chromatography until the chromatographic product gives a single spot by thin layer chromatography, thus producing 7 g of the target diphosphatidyl PEG 400 (yield: 25%).

The structure of the diphosphatidyl PEG 400 was confirmed by NMR, IR, and elemental analysis. The data obtained by the analysis were as follows:

$1_{H\text{-}NMR}$ (FIG. 1) [270 MHz: product of Japan Electronic Co., Ltd.; CDCl$_3$, TMS base, ppm]0.9(t, 12H, a), 1.3(bs, 96H, b), 1.6(m, 8H, c), 2.3(m, 8H, d), 3.7(bs, 32.5H, h), 4.0(m, 8H, g), 4.2(d-d, 2H, e), 4.4(d-d, 2H, e), 5.2(m, 2H, f)

|  | Elemental Analysis | | |
|---|---|---|---|
|  | C (%) | H (%) | P (%) |
| Calculated | 61.43 | 9.89 | 3.60 |
| Found | 61.32 | 9.88 | 3.50 |

Figure 2:
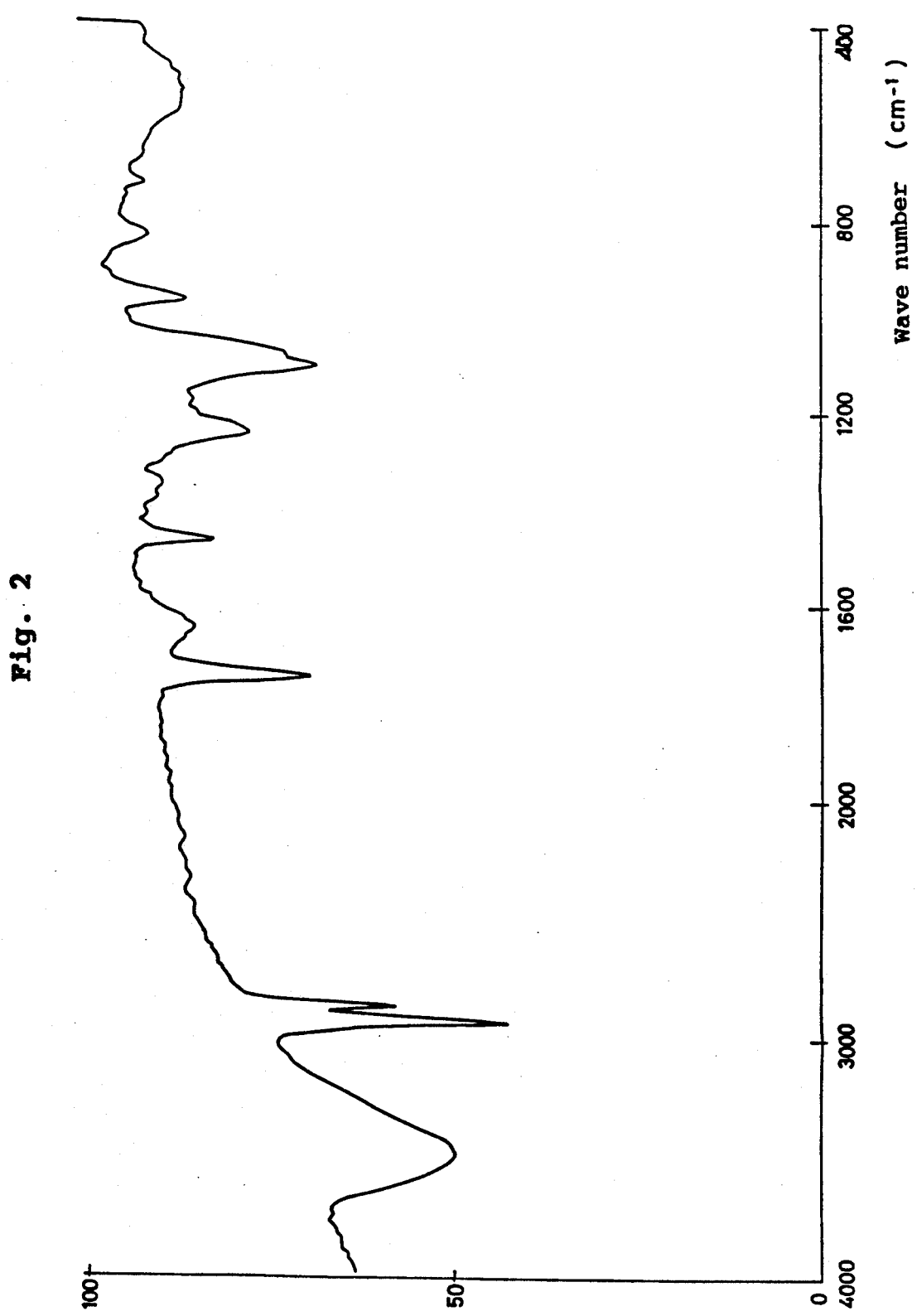

IR Spectrum: FIG. 2

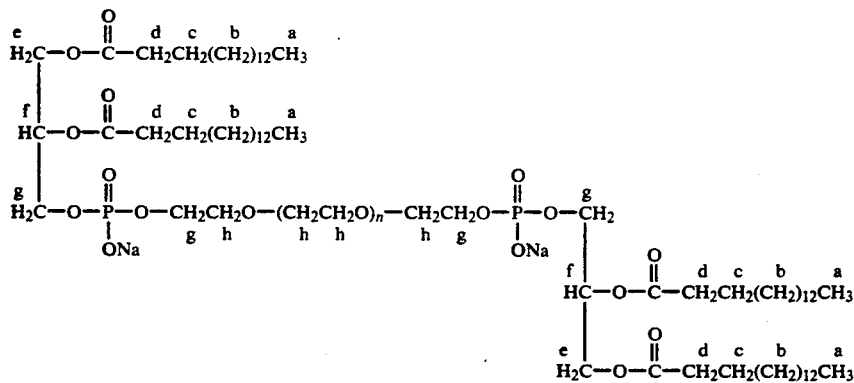

Example 2

Instead of dipalmitoyl phosphatidylcholine and PEG 400 of Example 1, 12 g of phosphatidylcholine derived from soybean (Epikuron 200, produced by Lukas Mayer Co.) and 25 g of PEG 600 (polyethylene glycol 600, produced by Wako Pure Chemical Co., Ltd.) were used. The same procedures as in Example 1 were followed to produce 10 g (yield: 32%) of diphosphatidyl PEG 600 having a fatty acid composition derived from soybean.

|  | Elemental Analysis | | |
|---|---|---|---|
|  | C (%) | H (%) | P (%) |
| Calculated | 61.62 | 9.31 | 3.09 |
| Found | 61.42 | 9.44 | 3.18 |

Example 3

Instead of dipalmitoyl phosphatidylcholine and PEG 400 of Example 1, 12 g of lecithin derived from yolk (PL-100H, produced by QP Co., Ltd.) and 12 g of PG 750 (polyglycerol #750, produced by Sakamoto Pharmaceutical Co., Ltd.) were used. The same procedures as in Example 1 were followed to produce 6.7 g (yield: 20%) of diphosphatidyl PG 750 having a fatty acid chain composition as derived from yolk.

|  | Elemental Analysis | | |
|---|---|---|---|
|  | C (%) | H (%) | P (%) |
| Calculated | 58.65 | 9.15 | 2.87 |
| Found | 58.78 | 9.27 | 2.98 |

Example 4

Glucose was dissolved into a 0.1 M sodium sulfate aqueous solution to prepare a glucose-salt aqueous solution of 0.056 M concentration. To 6 g of this solution was added 60 mg of a diphosphatidyl PEG 400-salt solution, and the mixture was heated over a water bath at a temperature of 50° C. while stirring using a magnetic stirrer until a homogeneous dispersion was obtained. The dispersion was allowed to cool to room temperature while stirring to produce a liposome solution which was pale blue in color and slightly turbid, but almost transparent. The average liposome particle diameter measured on this liposome solution using a particle size measuring device (Submicron Particle Size Analyzer, Model N4, product of Coulter Co.) was 82 nm. The liposome solution was stable without change at room temperature for a period of about one month.

The liposome solution was subjected to gel filtration at room temperature using Sephadex G50-Medium to separate liposomes and glucose which had not been incorporated into the liposomes. Concentrations of glucose and organic phosphorous compounds were quantitatively analyzed on the fraction in which liposomes were eluted. A trap volume of liposomes per mol of phosphorous atom contained in organic phosphorous compounds was 0.034 l/mol.

Example 5

Glucose was dissolved into a 0.02 M ammonium sulfate aqueous solution to prepare a glucose-salt aqueous solution of 0.056 M concentration. To 5 g of this solution was added 50 mg of a diphosphatidyl PEG 600, and the mixture was heated over a water bath at a temperature of 50° C. while stirring using a magnetic stirrer until a homogeneous dispersion was obtained. The dispersion was allowed to cool to room temperature while stirring to produce a liposome solution which was white in color and slightly turbid. The average liposome particle diameter measured on this liposome solution was 83 nm. The liposome solution was stable without change at room temperature for a period of two weeks.

The liposome solution was subjected to gel filtration in the same manner as in Example 4 and concentrations of glucose and organic phosphorous compounds were quantitatively analyzed on the fraction in which liposomes were eluted. A trap volume of liposomes per mol of phosphorous atom contained in organic phosphorous compounds was 0.033 l/mol.

Example 6

Liposome formation was observed under electron microscope. 30 g of white precipitates obtained in Example 4 was dissolved into 3 ml of 0.01 M ammonium sulfate solution. The liposomes in the solution was stained with a phosphorous-tungstic acid dye and observed under a transmission electron microscope. Liposomes having an average diameter of 94 nm were observed. The liposome diameter was in good agreement with that determined using the particle size measuring device.

Comparative Example 1

In the same manner as in Example 2, dipalmitoyl phosphatidylcholine, as a liposome forming agent, was mixed with a 0.056 M glucose-0.01 M ammonium sulfate aqueous solution, and the mixture was heated over a water bath at a temperature of 50° C. while stirring using a magnetic stirrer until a homogeneous dispersion was obtained. The dispersion was allowed to cool to room temperature while stirring to produce a liposome solution which was white in color and turbid.

The solution was allowed to stand at room temperature for 30 minutes to observe formation of white precipitates, demonstrating its poor stability. Particles having diameter of 1-5 $\mu$m were observed under optical microscope. No liposomes having a small particle size was observed.

Example 7

A liposome dispersion was prepared in the same manner as in Example 4 using 1% by weight of diphosphatidyl PPG 200 having a fatty acid chain composition derived from phospholipids of soybean, 0.02 M triethanolammonium chloride as a water soluble salt, and 0.056 M glucose as an active component.

The liposomes had an average diameter of 457 nm. Liposomes obtained by purification by gel filtration had a trap volume per mol of phosphorous atom of 0.23 l/mol.

Example 8

Thirty (30) mg of diphosphatidyl PEG 400 and 25 mg of sodium 2-decyltetradecylphosphate were dissolved into a 2:1 chloroform-methanol mixed solvent to prepare a homogeneous dispersion. The dispersion was distilled under reduced pressure to dryness to completely remove organic solvents. To the homogeneous solid thus obtained 3.5 g of a 0.167 M urea aqueous solution was added, and the mixture was heated over a water bath at a temperature of 50° C. while stirring using a magnetic stirrer until a homogeneous dispersion was obtained. The dispersion was allowed to cool to room temperature while stirring to produce a liposome solution which was pale blue in color and turbid, but had a considerable transparency. The liposomes had an average diameter of 359 nm.

The solution was subjected to gel filtration in the same manner as in Example 4. Phosphorous and urea were quantitatively analyzed on the fraction in which liposomes eluted. As a result, the liposomes obtained were found to have a trap volume per mol of phosphorous atom of 0.21 l/mol.

Example 9

Twelve (12) g of dipalmitoyl phosphatidylcholine, 4.8 g of sodium chloride, 25 g of polyethylene glycol having an average molecular weight of 400 (hereinafter referred to as PEG 400), 1,200 units of phospholipase D having a phosphatidyl group transfer activity (e.g. that derived from Actinomadura), 120 ml of diethylether, and 100 ml of water were charged into a reactor, and the mixture was stirred at 30° C. for 24 hours. After the reaction, chloroform and methanol were added to extract lipids. To 11.5 g of precipitates thus produced 200 ml of acetone was added, and the mixture was centrifuged to remove the precipitates. The solution was concentrated to dryness to obtain 9.9 g of white crystals.

To 50 mg of the white precipitates 5 g of a glucose-salt aqueous solution of 0.056 M concentration prepared by dissolving glucose into a 0.02 M sodium sulfate aqueous solution. The mixture was heated over a water bath at a temperature of 50° C. while stirring using a magnetic stirrer until a homogeneous dispersion was obtained. The dispersion was allowed to cool to room temperature while stirring to produce a white turbid liposome solution. The average liposome particle diameter measured on this liposome solution was 131 nm. The liposome solution was stable without change at room temperature for a period of two weeks.

The solution was subjected to gel filtration in the same manner as in Example 4. Glucose and phosphorous concentrations were quantitatively analyzed on the fraction in which liposomes eluted. As a result, the liposomes obtained were found to have a trap volume per mol of phosphorous atom of 0.22 l/mol.

The liposomes in the solution was stained with a phosphorous-tungstic acid dye and observed under a transmission electron microscope. Unilamella liposomes having an average diameter of 101 nm were observed. The liposome diameter was in good agreement with that determined using a particle size measuring device.

Example 10

Fifteen (15) g of dipalmitoyl phosphatidylcholine, 6.0 g of sodium chloride, 75 g of polyglycerol having an average molecular weight of 750, 1,500 units of phospholipase D having a phosphatidyl group transfer activity, 150 ml of diethylether, and 150 ml of water were charged into a reactor, and the mixture was stirred at 30° C. for 24 hours. After the reaction, the extraction and purification of the product were performed in the same manner as in Example 4 to produce 14.1 g of purified product.

A liposome dispersion was prepared in the same manner as in Example 9 using 1% by weight of the thus obtained white precipitates, 0.02 M aqueous ammonium sulfate as a water soluble salt, and 1% glycerol as an active component.

The liposomes had an average diameter of 145 nm. Liposomes had a trap volume per mol of phosphorous atom of 0.22 l/mol.

Example 11

A liposome dispersion was prepared in the same manner as in Example 9 using 1% by weight of a mixture prepared by the reaction of phosphatidylcholine having a fatty acid chain composition derived from soybean lipids and polypropylene glycol having an average molecular weight of 200 using phospholipase D having a phosphatidyl group transfer activity, 0.02 M triethanolammonium chloride as a water soluble salt, and 0.056 M glucose as an active component.

The liposomes had an average diameter of 247 nm. Liposomes obtained by purification by gel filtration had a trap volume per mol of phosphorous atom of 0.28 l/mol.

Example 12

A liposome dispersion was prepared in the same manner as in Example 9 using 1% by weight of white precipitate which were prepared by the reaction of dipalmitoyl phosphatidylcholine and PEG 400, 0.01 M equivalent sodium sulfate, and 0.056 M equivalent vitamin C as an active component.

The liposomes had an average diameter of 305 nm. Liposomes obtained by purification by gel filtration had a trap volume per mol of phosphorous atom of 0.31 l/mol.

Example 13

Glucose was dissolved into 0.01 M sodium sulfate aqueous solution to a concentration of 0.056 M to prepare a glucose-salt solution. 6 g of this solution was added to 60 mg of white crystals, and the mixture was heated over a water bath at temperature of 50° C. while stirring using a magnetic stirrer until a homogeneous dispersion was obtained. The dispersion was allowed to cool to room temperature while stirring to produce a liposome solution which was pale blue in color and slightly turbid, but almost transparent. The average liposome particle diameter measured on this liposome solution using a particle size measuring device (Submicron Particle Size Analyzer, Model N4, product of Coulter Co.) was 88 nm. The liposome solution was stable without change at room temperature for a period of about one month.

The liposome solution was subjected to gel filtration at room temperature using Sephadex G50-Medium to separate liposomes and glucose which had not been incorporated into the liposomes. Concentrations of glucose and organic phosphorous compounds were quantitatively analyzed on the fraction in which liposomes were eluted. A trap volume of liposomes per mol of phosphorous atom contained in organic phosphorous compounds was 0.023 l/mol.

Example 14

A mixture of 0.61% by weight of a product produced by the reaction of phosphatidylcholine having a fatty acid composition derived from yolk and polyglycerol having an average molecular weight of 500 in the presence of phospholipase D having a phosphatidyl group transfer activity and 0.39% by weight of dipalmitoyl phosphatidylcholine as a surface active agent were dissolved into a 2:1 chloroform-methanol mixed solvent to prepare a homogeneous dispersion. The dispersion was distilled under reduced pressure to dryness. To the homogeneous solid thus obtained 0.133 M glycin, as an active component, was added, and the mixture was heated over a water bath at a temperature of 50° C. while stirring using a magnetic stirrer until a homogeneous dispersion was obtained. The dispersion was allowed to cool to room temperature while stirring to produce a liposome solution which was pale blue in color and turbid, but had a considerable transparency. The liposomes had an average diameter of 271 nm.

The solution was subjected to gel filtration in the same manner as in Example 4. Phosphorous and urea were quantitatively analyzed on the fraction in which liposomes eluted. As a result, the liposomes obtained were found to have a trap volume per mol of phosphorous atom of 0.16 l/mol.

Example 15

A 0.01 M ammonium sulfate aqueous solution was prepared. Glucose was dissolved into this solution to a concentration of 0.056 M to prepare a glucose-salt solution. 6 g of this solution was added to 60 mg of dipalmitoyl phosphatidylglucose (hereinafter referred to as DPP-glucose) which was prepared in the same manner as in Example 1 except for using glucose instead of PEG 400. The mixture was heated over a water bath at a temperature of 50° C. while stirring using a magnetic stirrer until a homogeneous dispersion was obtained. The dispersion was allowed to cool to room temperature while stirring to produce a white, turbid liposome solution. The average liposome particle diameter measured on this liposome solution was 380 nm. The liposome solution was stable without change at room temperature for a period of about two weeks.

The liposome solution was subjected to gel filtration in the same manner as in Example 4 and a glucose concentration and a DPP-glucose concentration were determined on the fraction in which liposomes were eluted to find that the concentrations of glucose and DPP-glucose were respectively $5.1 \times 10^{-5}$ M and $5.8 \times 10^{-3}$ M. Based on these results, the liposomes obtained were determined to have a trap volume per mol of phosphorous atom of 0.16 l/mol.

Example 16

Thirty (30) mg of DPP-glucose and 25 mg of sodium 2-decyltetradecylphosphate were dissolved into a 2:1 chloroform-methanol mixed solvent to prepare a homogeneous dispersion. The dispersion was distilled under reduced pressure to dryness. To the homogeneous solid thus obtained 3.5 g of a 0.167 M urea aqueous solution was added, and the mixture was heated over a water bath at a temperature of 50° C. while stirring using a magnetic stirrer until a homogeneous dispersion was obtained. The dispersion was allowed to cool to room temperature while stirring to produce a liposome solution which was pale blue in color and turbid, but had a considerable transparency. The liposomes had an average diameter of 240 nm.

The solution wa subjected to gel filtration in the same manner as in Example 4. Concentrations of phosphorous and urea were quantitatively analyzed on the fraction in which liposomes eluted. As a result, the respective concentrations of the phosphorous and the urea was found to be $1.3 \times 10^{-3}$ M and $2.4 \times 10^{-5}$ M. Based on these results, the liposomes obtained were determined to have a trap volume per mol of phosphorous atom of 0.11 l/mol.

Example 17

A homogeneous dispersion was prepared using 31 mg of dipalmitoyl phosphatidylsorbitol (hereinafter referred to as DPP-sorbitol) which was prepared in the same manner as in Example 1 but for using sorbitol instead of PEG 400 and dissolving this DPP-sorbitol into a 2:1 chloroform-methanol mixed solvent. The mixture was heated over a water bath at a temperature of 50° C. while stirring using a magnetic stirrer until a homogeneous dispersion was obtained. The dispersion was allowed to cool to room temperature while stirring to produce a liposome solution which was pale blue in color and slightly turbid, but almost transparent. The average liposome particle diameter measured on this liposome solution was 125 nm.

The liposome solution was subjected to gel filtration in the same manner as in Example 1. Concentrations of phosphorous and urea were quantitatively analyzed on the fraction in which liposomes eluted. As a result, the respective concentrations of the phosphorous and the urea was found to be $4.0 \times 10^{-3}$ M and $2.1 \times 10^{-4}$ M. Based on these results, the liposomes obtained were determined to have a trap volume per mol of phosphorous atom of 0.95 l/mol.

Examples 18-19, Comparative Examples 2-3

Lotions having formulations given in Table 1 were prepared using phosphates prepared in Example 9 (Example 18) and Example 10 (Example 18). The lotions were tested for their moisturizing effects. The results are shown in Table 2.

TABLE 1

| Components | Examples | | (% by weight) Comparative Examples | |
|---|---|---|---|---|
| | 18 | 19 | 2 | 3 |
| Phosphate of Example 9 | 0.1 | — | — | — |
| Phosphate of Example 10 | — | 0.1 | — | — |
| Sodium Sulfate | 0.5 | 0.5 | — | 0.5 |
| Glycerol | 5.0 | 5.0 | 5.0 | 5.0 |
| 1,3-butylene glycol | 2.0 | 2.0 | 2.0 | 2.0 |
| PEG 1500 | 1.0 | 1.0 | 1.0 | 1.0 |
| POE (4.0) hydrogenated castor oil | 1.0 | 1.0 | 1.0 | 1.0 |
| Ethanol | 10.0 | 10.0 | 10.0 | 10.0 |
| Methyl paraben | 0.3 | 0.3 | 0.3 | 0.3 |
| Perfume | 0.1 | 0.1 | 0.1 | 0.1 |
| DPPC* | — | — | — | 0.1 |
| Purified water | Balance | Balance | Balance | Balance |

*DPPC: dipalmitoyl phosphatidylcholine

Preparation Method

Sodium sulfate was dissolved into purified water. To the solution glycerol was added to dissolve. This solution was added to white precipitates of the organic phosphate and the mixture was heated over a water bath at a temperature of about 50° C. with stirring to produce a liposome phase. Separately, a water phase was prepared by adding and dissolving 1,3-butylene glycol and polyethylene glycol 1500 into purified water at room temperature. A solution prepared by adding and dissolving the surface active agent, antiseptic, and perfume into ethanol was added to the water phase and dissolved. To this the liposome phase was added and the mixture was filtered to prepare a lotion.

Test Method

A prescribed amount of the lotion was applied to inside of forearms. After having been left for 3 hours, the site to which the lotion was applied was washed with warm water. The subject stayed in a thermostat room of a 20° C. temperature and 50% humidity for 3 hours, after which the water content of the horny layer was measured using an impedance meter (product of IBS Co.). The average values (n=5) are given in Table 2.

TABLE 2

| | Examples | | Comparative Examples | |
|---|---|---|---|---|
| | 18 | 19 | 2 | 3 |
| Moisturizing Effects | 60 | 66 | 17 | 38 |

As evident from Table 2, lotions of the present invention, to which phosphate (a) capable of producing stable small liposomes was added, exhibited more excellent moisture-retaining effect than comparative lotions to which no such a phosphate was added.

Example 20-21, Comparative Example 3

The cosmetics having formulations listed in Table 3 were produced using the phosphate mixture obtained in Example 2 according to the method described below, and subjected to organoleptic evaluation.

TABLE 3

| Component | Examples | | Comparative Example |
|---|---|---|---|
| | 20 | 21 | 3 |
| Phosphate mixture prepared in Example 2 | 10.0 | 20.0 | — |
| Glycerol (86%) | 5.0 | 5.0 | 5.0 |
| 1,3-butylene glycol | 3.0 | 3.0 | 3.0 |
| DGMI | — | 2.0 | — |
| Squalane | — | 2.0 | — |
| Olive oil | — | 6.0 | — |
| Octyldodecyl myristate | — | 2.0 | — |
| POE (40 EO) hydrogenated castor oil | — | — | 0.1 |
| Ethanol (55%) | 8.0 | 8.0 | 8.0 |
| Methylparaben | 0.1 | 0.1 | 0.1 |
| Lactic acid | 0.02 | 0.02 | 0.02 |
| Perfume | 0.05 | 0.05 | 0.05 |
| Purified water | Balance | Balance | Balance |

Preparation Method

Cosmetics were produced based on the formulations listed in Table 3. The cosmetic of Example 20 was produced as follows. The phosphate mixture, glycerol, and lactic acid were added to purified water. The mixture was heated at 50° C. with stirring and cooled to room temperature. To the water phase obtained was slowly added an ethanol phase prepared by adding 1,3-butylene glycol, POE (40 EO) hydrogenated castor oil, metylparaben, and the perfume to ethanol to obtain a transparent jelly cosmetic. The cosmetic of Example 21 was produced as follows. The mixture of phosphate esters, DGMI, squarane, olive oil, and Octyldodecyl myristate were mixed with stirring. To a oil phase obtained a water phase prepared by adding glycerol, and lactic acid to the purified water, and an ethanol phase prepared by adding POE (40 EO) hydrogenated castor oil, 1,3-butylene glycol, methylparaben, and the perfume to ethanol were slowly added followed by stirring to obtain a semitransparent jelly cosmetic. The cosmetic of Comparative Example 3 was produced in the same manner as in Example 20.

The cosmetic of Example 20 which formed a transparent jelly had more excellent extensibility and moisturized feeling than conventional cosmetics when using. The cosmetic of Example 21 which formed a semitransparent jelly gave a moisturized feeling without stickiness when using.

Example 22-23, Comparative Example 4

The cosmetics having formulations listed in Table 4 were produced using the phosphate mixture prepared in Example 1 or Example 2 according to the method described below, and subjected to organoleptic evaluation.

TABLE 4

| Component | Examples 22 | Examples 23 | Comparative Example 4 |
|---|---|---|---|
| Phosphate mixture prepared in Example 1 | 25.0 | — | — |
| Phosphate mixture prepared in Example 2 | — | 10.0 | — |
| Glycerol (86%) | 8.0 | 10.0 | 5.0 |
| 1,3-butylene glycol | 8.0 | 10.0 | 5.0 |
| DGMI | 10.0 | 15.0 | 5.0 |
| Squalane | 10.0 | 15.0 | 20.0 |
| Olive oil | 5.0 | 5.0 | 5.0 |
| Octyldodecyl myristate | 1.0 | 5.0 | 5.0 |
| POE (40 EO) hydrogenated castor oil | — | — | 5.0 |
| Ethanol (55%) | 5.0 | 5.0 | 5.0 |
| Methylparaben | 0.1 | 0.1 | 0.1 |
| Lactic acid | 0.02 | 0.02 | 0.02 |
| Perfume | 0.05 | 0.05 | 0.05 |
| Purified water | Balance | Balance | Balance |

Preparation Method

Cosmetics were produced based on the formulations listed in Table 4. Cosmetics of Example 22 and Example 23 were produced as follows. To a oil phase prepared by mixing the phosphate mixture, DGMI, squarane, olive oil, and octyldodecyl myristate followed by stirring, a water phase prepared by adding glycerol, lactic acid, 1,3-butylene glycol, methylparaben, perfume, and ethanol to the purified water was slowly added dropwise followed by stirring to produce a creamy cosmetic. The cosmetic of Comparative Example 4 was produced in the same manner as in the above examples.

The cosmetics of Example 22 and Example 23 had excellent extensibility, and moisturized and fresh feeling when using.

Obviously, numerous modifications and variations of the present invention are possible in light of the above teachings. It is therefore to be understood that within the scope of the appended claims, the invention may be practiced otherwise than as specifically described herein.

What is claimed is:

1. A liposome comprising as its membrane constituents a monophosphate represented by the formula (I) or a diphosphate represented by the formula (II), or both,

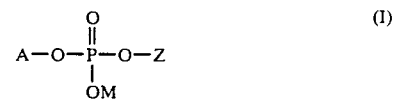

wherein A represents the following group (i), (ii), or a mixture thereof,

wherein $R^1$ and $R^2$ may be the same or different and individually represent a group $-OCOR^3$, $-OR^4$, or a mixture thereof, wherein $R^3$ and $R^4$ may be the same or different and individually represent an alkyl or alkenyl group having 6-32 carbon atoms, or $R^1$ and $R^2$ may together form the group,

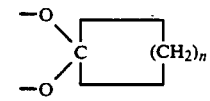

wherein n is an integer of 11-19; M represents a hydrogen atom, an alkali metal, an alkaline earth metal, an ammonium, alkylammonium, or alkanolammonium group, and Z represents a residue of one of the following groups (1) or (2) from which one primary hydroxyl group is removed, (1) a mono- or polyether group represented by the formula $HO-(Y-O-)_m-H$, wherein m is an integer of 2-50 and Y represents an alkylene or substituted alkylene group having 2-4 carbon atoms, (2) a polyglycerol group having a condensation degree of 2-50;

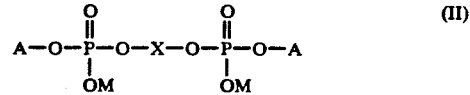

wherein A and M have the same meaning as defined in formula (I), and X represents a residue of one of the following groups (1) or (2) from which two primary hydroxyl groups are removed, (1) a mono- or polyether group represented by the formula $HO-(Y-O-)_m-H$, wherein m is an integer of 2-50 and Y represents an alkylene or substituted alkylene group having 2-4 carbon atoms, (2) a polyglycerol group having a condensation degree of 2-50.

2. A liposome which is prepared by mixing in an aqueous solution:

(a) a monophosphate represented by the formula (I) or a diphosphate represented by the formula (II), or both,

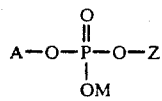 (I)

wherein A represents the following group (i), (ii) or a mixture thereof,

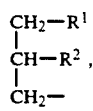 (i)

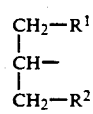 (ii)

wherein $R^1$ and $R^2$ may be the same or different and individually represent a group $-OCOR^3$, $-OR^4$, or a mixture thereof, wherein $R^3$ and $R^4$ may be the same or different and individually represent an alkyl or alkenyl group having 6–32 carbon atoms, or $R^1$ and $R^2$ may together form the group,

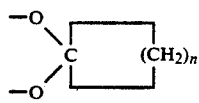

wherein n is an integer of 11-19; M represents a hydrogen atom, an alkali metal, an alkaline earth metal, an ammonium, alkylammonium, or alkanolammonium group; and Z represents a residue of one of the following groups (1) or (2) from which one hydroxyl group is removed,
(1) a mono- or polyether group represented by the formula HO—(y—O—)$_m$—H, wherein m is an integer of 2–50 and Y represents an alkylene or substituted alkylene group having 2–4 carbon atoms,
(2) a polyglycerol group having a condensation degree of 2–50;

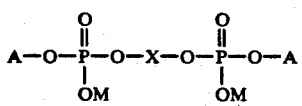 (II)

wherein A and M have the same meaning as defined in formula (I), and X represents a residue of one of the following groups (1) or (2) from which two primary hydroxyl groups are removed,
(1) a mono- or polyether group represented by the formula HO—(y—O—)$_m$—H, wherein m is an integer of 2–50 and Y represents an alkylene or substituted alkylene group having 2–4 carbon atoms,
(2) a polyglycerol group having a condensation degree of 2–50; and
(b) a water-soluble salt or a surface active agent, or both; and optionally (c) a cosmetically or medicinally acceptable active component.

3. A liposome according to claim 1 or claim 2 having an average particle diameter of not more than 500 nm.

4. A cosmetic composition comprising a monophosphate represented by the formula (I) or a diphosphate represented by the formula (II), or both,

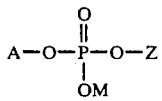 (I)

wherein A represents the following group (i), (ii), or a mixture thereof,

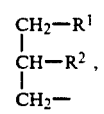 (i)

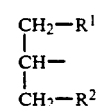 (ii)

wherein $R^1$ and $R^2$ may be the same or different and individually represent a group $-OCOR^3$, $-OR^4$, or a mixture thereof, wherein $R^3$ and $R^4$ may be the same or different and individually represent an alkyl or alkenyl group having 6–32 carbon atoms, or $R^1$ and $R^2$ may together form the group,

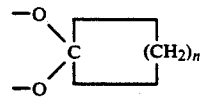

wherein n is an integer of 11-19; M represents a hydrogen atom, an alkali metal, an alkaline earth metal, an ammonium, alkylammonium, or alkanolammonium group; and Z represents a residue of one of the following groups (1) or (2) from which one primary hydroxyl group is removed,
(1) a mono- or polyether group represented by the formula HO—(Y—O—)$_m$—H, wherein m is an integer of 2–50 and Y represents an alkylene or substituted alkylene group having 2–4 carbon atoms,
(2) a polyglycerol group having a condensation degree of 2–50;

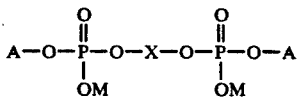 (II)

wherein A and M have the same meaning as defined in formula (I), and X represents a residue of one of the following groups (1) or (2) from which two primary hydroxyl groups are removed,
(1) a mono- or polyether group represented by the formula HO—(y—O—)$_m$—H, wherein m is an integer of 14 50 and Y represents an alkylene or substituted alkylene group having 2–4 carbon atoms, (2) a polyglycerol group having a condensation degree of 2-50; and a cosmetically acceptable active component.

5. A liposome preparation comprising a liposome which comprises as its membrane constituents a monophosphate represented by the formula (I), or a diphosphate represented by the formula (II), or both,

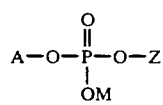   (I)

wherein A represents the following group (i), (ii), or a mixture thereof,

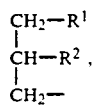   (i)

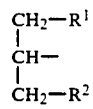   (ii)

wherein $R^1$ and $R^2$ may be the same or different and individually represent a group $—OCOR^3$, $—OR^4$, or a mixture thereof, wherein $R^3$ and $R^4$ may be the same or different and individually represent an alkyl or alkenyl group having 6-32 carbon atoms, or $R^1$ and $R^2$ may together form the group,

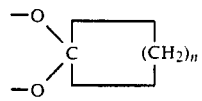

wherein n is an integer of 11-19; M represents a hydrogen atom, an alkali metal, and alkaline earth metal, an ammonium, alkylammonium, or alkanolammonium group; and Z represents a residue of one of the following groups (1) or (2) from which one primary hydroxyl group is removed, (1) a mono- or polyether group represented by the formula $HO—(Y—O—)_m—H$, wherein m is an integer of 2-50 and Y represents an alkylene or substituted alkylene group having 2-4 carbon atoms, (2) a polyglycerol group having a condensation degree of 2-50;

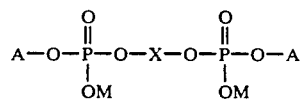   (II)

wherein A and M have the same meaning as defined in formula (I), and X represents a residue of one of the following groups (1) or (2) from which two primary hydroxyl groups are removed, (1) a mono- or polyether group represented by the formula $HO—(Y—O—)_m—H$, wherein m is an integer of 2-50 and Y represents and alkylene or substituted alkylene group having 2-4 carbon atoms, (2) a polyglycerol group having a condensation degree of 2-50; and a cosmetically or medicinally acceptable active component.

* * * * *